(12) United States Patent
Culbert

(10) Patent No.: US 7,175,625 B2
(45) Date of Patent: Feb. 13, 2007

(54) SOFT TISSUE ANCHOR AND METHOD OF USING SAME

(75) Inventor: Brad S. Culbert, Rancho Santa Margarita, CA (US)

(73) Assignee: Triage Medical, Irvine, CA (US)

( * ) Notice: Subject to any disclaimer, the term of this patent is extended or adjusted under 35 U.S.C. 154(b) by 0 days.

(21) Appl. No.: 10/719,086

(22) Filed: Nov. 21, 2003

(65) Prior Publication Data
US 2004/0106925 A1 Jun. 3, 2004

Related U.S. Application Data

(60) Provisional application No. 60/428,847, filed on Nov. 25, 2002.

(51) Int. Cl.
*A61B 17/58* (2006.01)
(52) U.S. Cl. ...................................................... 606/73
(58) Field of Classification Search .................. 606/60, 606/65, 232, 71–73; 411/340, 348, 396
See application file for complete search history.

(56) References Cited

U.S. PATENT DOCUMENTS

| | | | |
|---|---|---|---|
| 4,940,467 A | 7/1990 | Tronzo | |
| 4,988,351 A * | 1/1991 | Paulos et al. | 606/72 |
| 5,013,315 A | 5/1991 | Barrows | |
| 5,013,316 A | 5/1991 | Goble et al. | |
| 5,167,664 A | 12/1992 | Hodorek | |
| 5,217,462 A | 6/1993 | Asnis et al. | |
| 5,370,661 A | 12/1994 | Branch | |
| 5,520,690 A * | 5/1996 | Errico et al. | 606/61 |
| 5,545,164 A * | 8/1996 | Howland | 606/61 |
| D374,287 S * | 10/1996 | Goble et al. | D24/145 |
| 5,643,320 A | 7/1997 | Lower et al. | |
| 5,735,853 A * | 4/1998 | Olerud | 606/71 |
| 5,954,722 A * | 9/1999 | Bono | 606/61 |
| 6,123,711 A * | 9/2000 | Winters | 606/73 |
| 6,162,234 A | 12/2000 | Freedland et al. | |
| 6,319,254 B1 | 11/2001 | Giet et al. | |
| 6,511,481 B2 | 1/2003 | Von Hoffmann et al. | |
| 6,582,453 B1 | 6/2003 | Tran et al. | |
| 6,585,730 B1 | 7/2003 | Foerster | |
| 6,605,096 B1 | 8/2003 | Ritchart | |
| 2002/0143335 A1 | 10/2002 | von Hoffmann et al. | |

* cited by examiner

*Primary Examiner*—Eduardo C Robert
(74) *Attorney, Agent, or Firm*—Knobbe, Martens, Olson & Bear, LLP.

(57) ABSTRACT

A soft tissue anchor device and methods of installing the soft tissue anchor device are disclosed. The device has an elongate body having a proximal end and a distal end. There is a helical anchor on the distal end. A retention structure is provided on the body, proximal to the anchor. The device also includes a proximal anchor, moveably carried by the body. The device includes an adjustable flange that is configured to receive the proximal anchor. The proximal anchor is configured to be rotational with respect to the flange. The adjustable flange is configured to be positioned at a variable angle with respect to the body. The proximal anchor is moveable in the distal direction with respect to the body and the retention structure resists proximal movement of the proximal anchor with respect to the body.

17 Claims, 5 Drawing Sheets

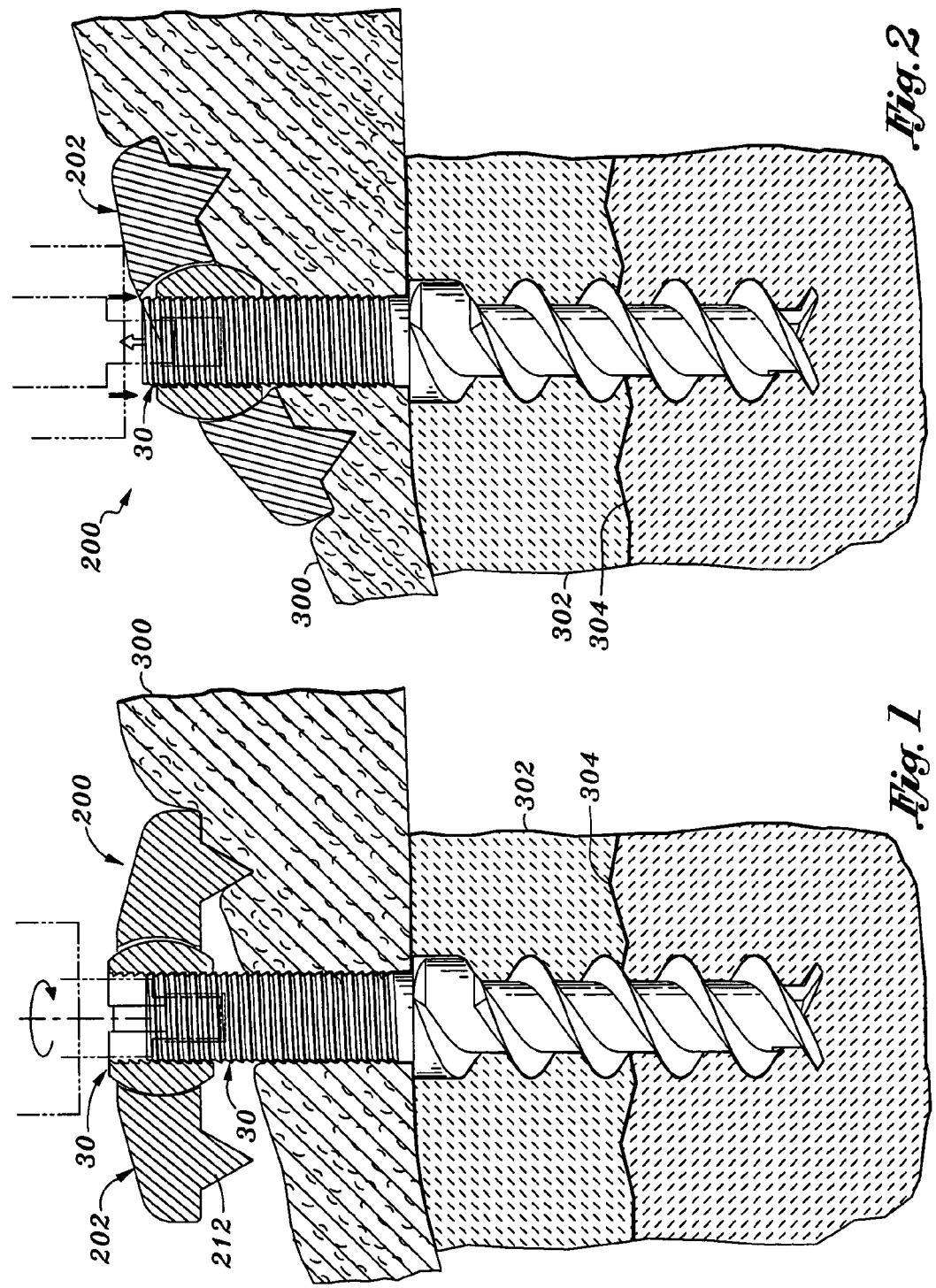

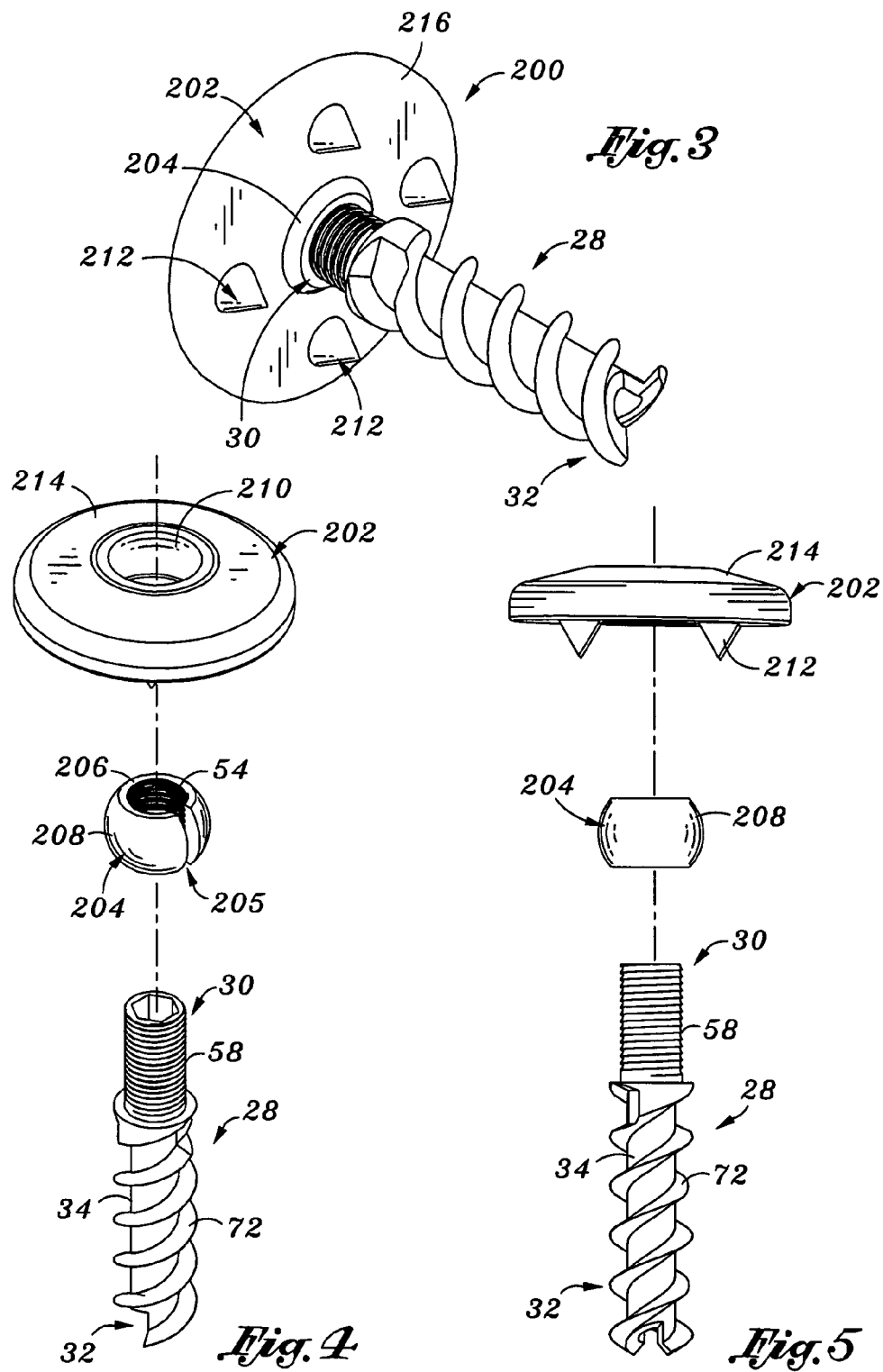

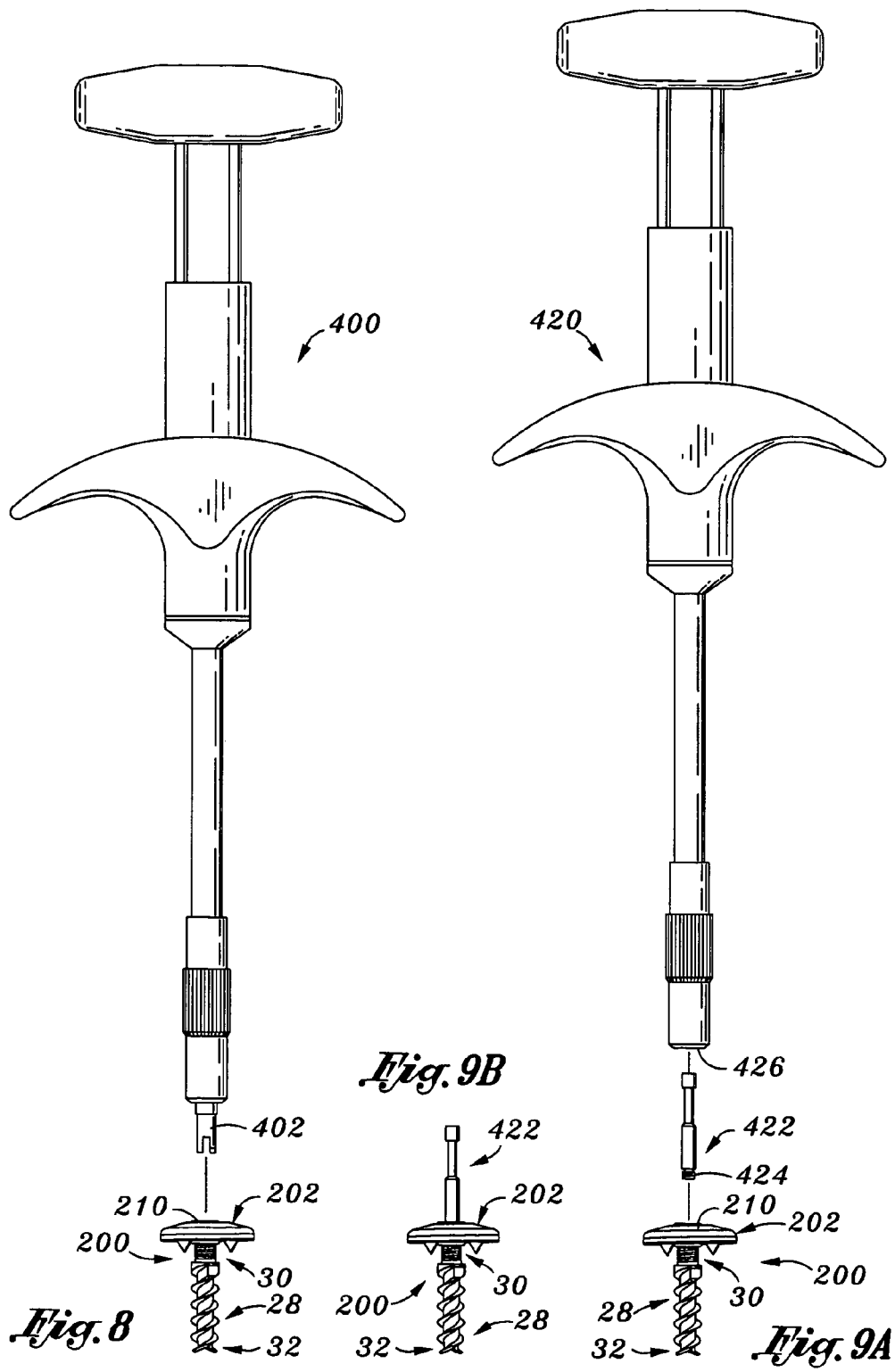

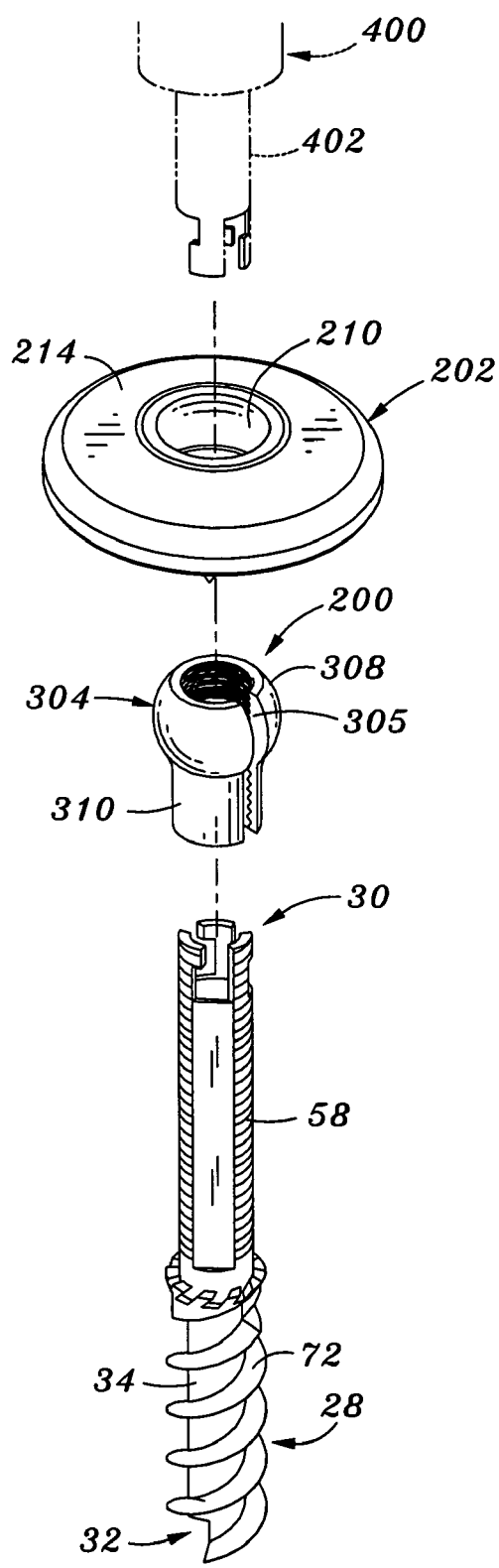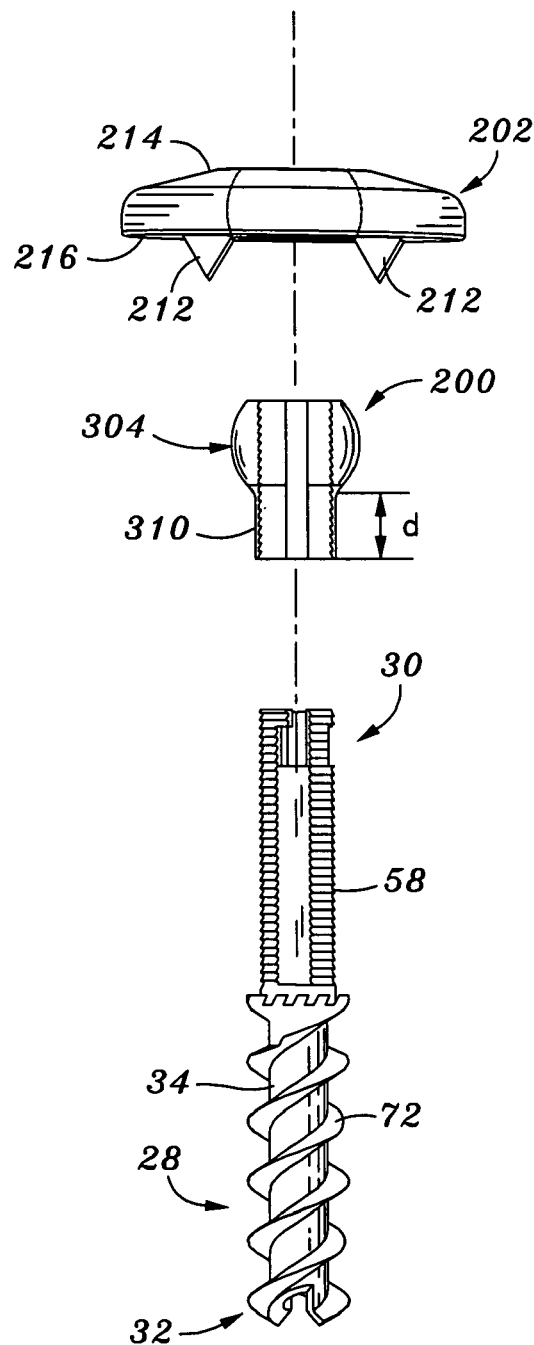

SOFT TISSUE ANCHOR AND METHOD OF USING SAME

CROSS-REFERENCE TO RELATED APPLICATIONS

This application claims the benefit of U.S. Provisional Application 60/428,847, filed Nov. 25, 2002, the entire contents of which are hereby incorporated by reference.

STATEMENT RE: FEDERALLY SPONSORED RESEARCH/DEVELOPMENT

Not Applicable

BACKGROUND OF THE INVENTION

The present invention relates generally to surgical devices and more particularly to a soft tissue anchor with an axially moveable and locking flange and methods of using same.

A variety of elongated implants (nail, screw, pin, etc.) have been developed to attach soft tissue (e.g., a ligament or a tendon) to hard tissue (e.g., a bone). The elongated implants may be secured with sutures. Typically, such devices attach the tissue to the bone by rotating the fixation device until the tissue is firmly fixed to the bone. However, as the device is tightened, the tissue tends to rotate, particularly with the final tightening cinch.

Thus, there is a need for a fixation device that provides for fixation of soft-tissue (e.g., tendon or ligament) to bone without rotating the soft tissue.

BRIEF SUMMARY OF THE INVENTION

A soft tissue anchor device and methods of installing the soft tissue anchor device are disclosed. The device has an elongate body having a proximal end and a distal end. There is a helical anchor on the distal end. A retention structure is provided on the body, proximal to the anchor. The device also includes a proximal anchor, moveably carried by the body. The device includes an adjustable flange that is configured to receive the proximal anchor. The proximal anchor is configured to be rotational with respect to the flange. The adjustable flange is configured to be positioned at a variable angle with respect to the body. The proximal anchor is moveable in the distal direction with respect to the body and the retention structure resists proximal movement of the proximal anchor with respect to the body.

Upon installation of the soft tissue anchor device, the soft tissue anchor device attaches a soft tissue to a hard tissue and the flange retains the soft tissue anchor in the hard tissue preventing proximal or distal movement of the soft tissue anchor device.

The flange includes a distal (underside) surface and a proximal (top) surface. The flange may include at least one spike protruding from the distal surface of the flange. The flange may include a plurality of spikes spaced around the perimeter of the flange. The spikes may be spaced equidistantly relative to each other around the perimeter of the flange.

The body may be cannulated.

The flange preferably includes a flange recess configured to be engageable with an installation tool. There may also be a removable rotation member having a proximal end configured to removably engage with flange recess and a distal end configured to removably engage with an installation tool.

The elongate body may be made of titanium, a bioabsorbable polymeric material or a nonabsorbable polymeric material.

In one embodiment, the elongate body has a length in a range of about 10 mm to about 80 mm and a diameter in a range of 2 mm to about 6 mm, and the helical anchor has a major diameter in a range of about 3.5 mm to about 30 mm.

The method provides that a fixation device comprising a body having a first portion that forms a bone anchor and a removable portion that forms a proximal end is advanced through the tissue and into the bone. A bore may be provided, in which case the fixation device is advanced through the tissue into the bore in the bone. A proximal anchor of the fixation device is rotated so as to engage the bone anchor with the bone through the tissue. The proximal anchor is advanced distally along the fixation device and into an adjustable flange to install the fixation device. The flange is adjusted to secure the tissue to the bone.

Preferably, the flange is adjusted using a ratcheting motion.

The bore may be provided in the bone by self-tapping the fixation device. Alternatively, the bore may be provided in the bone by pre-drilling the bore.

BRIEF DESCRIPTION OF THE DRAWINGS

These as well as other features of the present invention will become more apparent upon reference to the drawings wherein:

FIG. 1 is a cross sectional view of an arrangement of a soft-tissue fixation device in a first (as installed) position;

FIG. 2 is a cross sectional view of the soft-tissue fixation device of FIG. 1 in a second (compressed) position where the flange is positioned on an angle;

FIG. 3 is a side perspective view of another side of the soft-tissue fixation device of FIG. 1;

FIG. 4 is an exploded perspective view of the soft-tissue fixation device of FIG. 1;

FIG. 5 is a side exploded view of the soft-tissue fixation device of FIG. 1;

FIG. 8 illustrates an exemplary tool that can be used to implant the fixation device of FIG. 1;

FIGS. 9A and 9B illustrate a variation of the tool and fixation device shown in FIG. 8;

FIG. 10 is a top perspective exploded view of an alternate embodiment of the fixation device; and FIG. 11 is a side exploded view of the fixation device shown in FIG. 10.

DETAILED DESCRIPTION OF THE INVENTION

Figure 6:
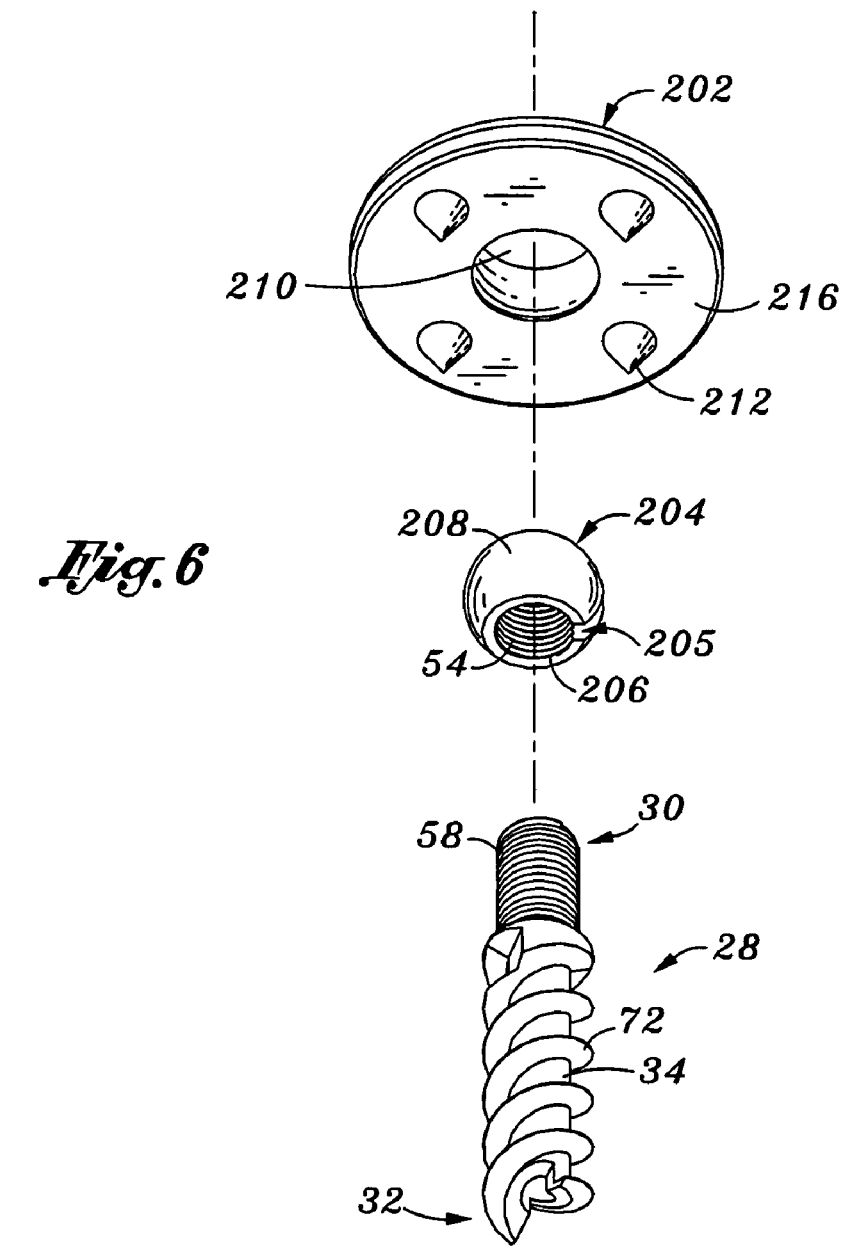
FIG. 6 is a bottom exploded perspective view of the soft-tissue fixation device of FIG. 1.

Referring now to the drawings wherein the showings are for purposes of illustrating preferred embodiments of the present invention only, and not for purposes of limiting the same, a soft tissue fixation device 200 is shown. FIG. 1 illustrates the fixation device 200 as installed (i.e., after placement attaching tissue to a bone). After installation, the fixation device 200 can be compressed and/or the flange 202 rotated (i.e., angled) as shown in FIG. 2. When the flange is compressed, it is retained in position such that the device does not move either distally or proximally. The length of the fixation device 200 is variable depending on the amount of compression used. Preferably, the compression is performed via ratcheting rather than rotation to avoid rotation of the tissue. As described more fully later, this compression can be performed using a ratcheting tool, such as the one shown in FIG. 8 or the one shown in FIGS. 9A and 9B. The fixation device 200 includes an adjustable flange 202 that may be angled as shown in FIG. 2. In exemplary embodiments, the flange 202 "floats" such that it automatically rotates to the optimal angle for the bone to which the soft tissue is being attached. Such flexibility (i.e., ability to adjust the flange to various positions) allows for stronger tissue-to-bone fixation and low profile.

The fixation device 200 of the present invention may be used to attach tissue or structure to the bone, such as in ligament reattachment and other soft tissue attachment procedures. The device may be used to repair a fracture 304 in which a soft tissue 300 is to be attached to the fractured bone 302. U.S. Patent Application Ser. No. 10/623,193 entitled "Method and Apparatus for Spinal Fixation" filed on Jul. 18, 2003 discloses a bone fixation device, various types of bone fractures and methods of repairing such fractures. The entire contents of this application are hereby expressly incorporated by reference. It will be appreciated that the device 200 can be used for any type of injury (including, but not limited to fractures) in which it is desirable to attach soft tissue 300 (such as a tendon or a ligament) to a hard tissue 302 (such as a bone). Plates and washers, with or without tissue spikes for soft tissue attachment, and other implants may also be attached to bone, using either resorbable or nonresorbable fixation devices depending upon the implant and procedure. The fixation device 200 may also be used to attach sutures to the bone, such as in any of a variety of tissue suspension procedures.

For example, peripheral applications for the fixation devices include utilization of the device for fastening soft tissue such as capsule, tendon or ligament to bone. The device 200 may also be used to attach a synthetic material such as marlex mesh, to bone or allograft material such as tensor fascia lata, to bone. In the process of doing so, retention of the material to bone may be accomplished with the collar, or the pin and or collar may be modified to accept a suture or other material for facilitation of this attachment.

Specific examples include attachment of the posterior tibial tendon to the navicular bone in the Kidner operation. This application may be accomplished using an appropriately sized implant of the present invention along with a washer with distally extending soft tissue spikes. Navicular-cuneiform arthrodesis may be performed utilizing the device 200 and concurrent attachment of the tendon may be accomplished. Attachment of the tendon may be accomplished in the absence of arthrodesis by altering the placement of the implant in the adjacent bone.

Ligament or capsule reattachment after rupture, avulsion or detachment, such as in the ankle, shoulder or knee can also be accomplished using the devices disclosed herein.

The cannulated design disclosed can be fashioned to accept an antibiotic impregnated rod for the slow adsorption of medication locally. This may be beneficial for prophylaxis, especially in open wounds, or when osteomyelitis is present and stabilization of fracture fragments is indicated.

A kit may be assembled for field use by military or sport medical or paramedical personnel. This kit contains an implanting tool, and a variety of implant device size and types. The kit may include additional components such as sterilization or disinfectant materials, a skin stapler, bandages, gloves, and basic tools for emergent wound and fracture treatment. Antibiotic rods may be included for wound prophylaxis during transport.

The soft tissue fixation device 200 comprises a body 28 extending between a proximal end 30 and a distal end 32. The proximal end 30 of the device 200 is provided with a proximal anchor 204. The proximal anchor 204 defines a tubular body or housing 206 and is axially distally moveable along the body 28. Complimentary locking structures 54, 58 on the housing 206 and the body 28 such as threads or ratchet-like structures resist proximal movement of the body 28 with respect to the anchor 204 under normal use conditions. As such, in some embodiments, the complimentary locking structures 54, 58 may permit the anchor 204 to be axially advanced along the body 28 by rotation. In some embodiments, the complimentary locking structures 54, 58 are generally rounded but include some flat surfaces (e.g., two opposing flat surfaces) alternating with curved or rounded surfaces. In such a case one locking structure may include some flat surfaces while the complementary locking surface is uniformly circular. In other embodiments, the complimentary locking structures 54, 58 may be uniformly circular. However, when attaching soft tissue to a bone, it is typically desirable to avoid such rotation as the rotation may cause the soft tissue 300 to be rotated. Preferably, the complimentary locking structures 54, 58 permit the anchor 204 to be axially advanced along the body 28 without rotation of the soft tissue.

Figure 7:
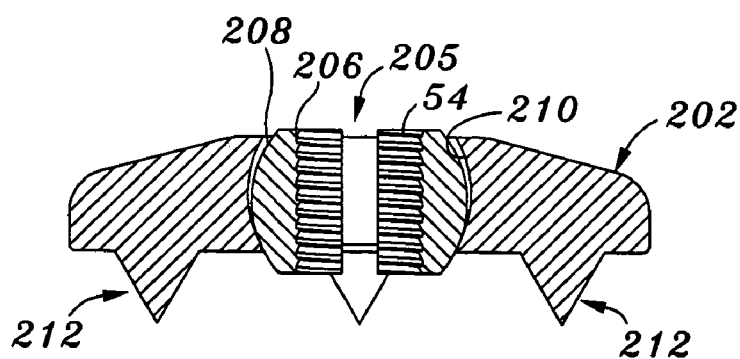
FIG. 7 is a cross-sectional view of the flange and proximal anchor of the soft-tissue fixation device of FIG. 1.

The illustrated proximal anchor 204 also includes a gap 205, 305 (see FIGS. 4, 6, 7 and 10) such that the illustrated anchor 204 forms a locking spherical split ring collar. In modified embodiments, the proximal anchor 204 can be formed without the gap 205.

The proximal anchor 204 preferably includes a smooth and more preferably rounded outer surface portion 208, which is configured to fit within a smooth and preferably rounded recessed portion 210 in the flange 202. In exemplary embodiments, the recessed portion 210 may actually be a hole. In such embodiments, a member having a recessed portion may be inserted in the hole. For example, as seen in FIG. 10, proximal end 30 may include a recess. Proximal end 30 fits through hole 210. In the embodiments shown in FIG. 10, the recess in the proximal end 30 is engageable with gripping member 402 of an insertion tool 400.

When the proximal anchor 204 is positioned in the flange 202, the flange 202 resists distal movement of the proximal anchor 204 while permitting at least limited rotation between the proximal anchor 204 and the flange 202. As such, the illustrated arrangement allows for angular movement of the flange 202 over the anchor 204 to accommodate variable anatomical angles of the bone surface.

In the illustrated embodiment, the flange 202 includes a plurality of spikes 212. The spikes 212 provide additional gripping support especially when the flange 202 is positioned against soft tissue. However, it should be appreciated that in modified embodiments the flange 202 may be formed without the spikes 212.

The length, diameter and construction materials of the body 28 can be varied, depending upon the intended clinical application. In embodiments optimized for various fractures or other injuries in an adult human population, the body 28 will generally be within the range of from about 10 mm to about 80 mm in length after sizing, and within the range of from about 2 mm to about 6 mm in maximum diameter. The major diameter of the helical anchor may be within the range of from about 3.5 mm to about 30 mm. In general, the appropriate dimensions of the body 28 will vary, depending upon the specific fracture or injury.

In one embodiment, the body 28 comprises titanium. However, as will be described in more detail below, other metals or bioabsorbable or nonabsorbable polymeric materials may be utilized, depending upon the dimensions and desired structural integrity of the finished fixation device 200. The distal end 32 of the body 28 is provided with a cancellous bone anchor or distal cortical bone anchor 34. Additional details of the distal bone anchor are described below.

The present invention can be implanted with minimally invasive procedures. For example, the fixation device 200 can be implanted arthroscopically. A bore may be pre-drilled in the hard tissue 302 prior to insertion of the fixation device 200. However, the fixation device 200 is preferably self-tapping so that no pre-drilling is required.

With reference to FIGS. 4 and 5, the proximal anchor 204 is pre-loaded into the flange 202. The body is then inserted into the member comprising the proximal anchor 204 and the flange 202. In exemplary embodiments, such as the one shown in FIGS. 10 and 11, the proximal anchor 304 includes an extension member 310. This extension member allows for a greater range of compression. The body 28 is inserted into the proximal anchor 204/flange 202 such that the body 28 is recessed with respect to the proximal anchor 204/flange 202 as shown in FIG. 1. Preferably, when the fixation device 200 is compressed (as shown in FIG. 2), the body 28 does not protrude through the flange 202 (i.e., the body 28 is flush or recessed with respect to the proximal surface 214 of the flange 202. This configuration requires a counterbore into the bone 302 slightly larger than the diameter and length d of the extension member 310 to allow the extension member 310 to seat into the bone 302.

With particular reference to FIG. 9B, the proximal end 30 of the body 28 may be provided with a rotational coupling 422, for allowing the body 28 to be rotationally coupled to a rotation device 420. The proximal end 30 of the body 28 may be desirably rotated to accomplish one or two discrete functions. In one application of the invention, the proximal end 30 is rotated to remove the rotational coupling 422 following tensioning of the device. Rotation of the rotational coupling 422 may also be utilized to rotationally drive the distal anchor into the bone. Any of a variety of rotation devices may be utilized, such as electric drills or hand tools (such as those shown in FIGS. 8 and 9A), which allow the clinician to manually rotate the proximal end 30 of the body. Thus, the rotational coupling 422 may have any of a variety of cross sectional configurations, such as one or more flats or splines.

In one embodiment, the rotational coupling 422 comprises a proximal projection of the body 28 having an axial recess with a polygonal cross section, such as a hexagonal cross section. The rotational coupling 422 may be a female component, machined or milled or attached to the proximal end 30 of the body 28. The rotational coupling may also be in the form of a male element, such as a hexagonal or other noncircular cross sectioned projection.

As illustrated, the body 28 is cannulated to accommodate installation over a placement (e.g., guide) wire as is understood in the art. The cross section of the illustrated central cannulation is circular but in other embodiments may be non circular, e.g., hexagonal, to accommodate a corresponding male tool for installation or removal of a removable portion 422 of the body 28. In other embodiments, the body 28 may be partially or wholly solid.

In the embodiments illustrated herein, the distal anchor 34 comprises a helical locking structure 72 for engaging cancellous and/or distal cortical bone. In the illustrated embodiment, the locking structure 72 comprises a flange that is wrapped around the axial lumen. The flange extends through at least one and generally from about two to about 50 or more full revolutions depending upon the axial length of the distal anchor and intended application. In exemplary fixation devices, the flange will generally complete from about 2 to about 20 revolutions. The helical flange 72 is preferably provided with a pitch and an axial spacing to optimize the retention force within cancellous bone, to optimize compression of the fracture.

The helical flange 72 of the illustrated embodiment has a generally triangular cross-sectional shape. However, it should be appreciated that the helical flange 72 can have any of a variety of cross sectional shapes, such as rectangular, oval or other as deemed desirable for a particular application through routine experimentation in view of the disclosure herein. The outer edge of the helical flange 72 defines an outer boundary. The ratio of the diameter of the outer boundary to the diameter of the central lumen can be optimized with respect to the desired retention force within the cancellous bone and giving due consideration to the structural integrity and strength of the distal anchor 34. Another aspect of the distal anchor 34 that can be optimized is the shape of the outer boundary and the central core, which in the illustrated embodiment are generally cylindrical.

A variety of other arrangements for the distal anchor 32 can also be used. For example, the various distal anchors described in U.S. Pat. No. 6,511,481, filed Mar. 30, 2001, and co-pending U.S. patent application Ser. No. 10/012,687, filed Nov. 13, 2001 can be incorporated into the fixation device 12 described herein. The entire contents of these applications are hereby expressly incorporated by reference. In particular, the distal anchor 32 may comprise a single helical thread surrounding a central core, much as in a conventional screw, which has been cannulated to facilitate placement over a wire. Alternatively, a double helical thread may be utilized, with the distal end of the first thread rotationally offset from the distal end of the second thread. The use of a double helical thread can enable a greater axial travel for a given degree of rotation and greater retention force than a corresponding single helical thread. Specific distal anchor designs can be optimized for the intended use, taking into account desired performance characteristics, the integrity of the distal anchor, and whether the distal anchor is intended to engage exclusively cancellous bone or will also engage cortical bone.

To rotate the proximal collar, the flange 202 is preferably provided with a gripping structure to permit an insertion tool (such as the one shown in FIG. 8 or the one shown in FIGS. 9A and 9B) to rotate the flange 202. Any of a variety of gripping structures may be provided, such as one or more slots, flats, bores or the like. In one embodiment, the flange 202 is provided with a circular recess 210. In other embodiments, the flange 202 is provided with a polygonal recess, such as a pentagonal or hexagonal recess 210. The recess 210 may be in the flange or the flange may have a hole 210 and the proximal anchor which is inserted through the hole 210 may include a recess.

The fixation device may be installed by pre-drilling. In such installations, the clinician first identifies a patient having an injury, such as a fracture, to be treated, which is fixable by an internal fixation device. As described in the U.S. Patent Application Ser. No. 10/623,193 entitled "Method and Apparatus for Spinal Fixation" filed on Jul. 18, 2003, the clinician accesses the injury, reduces the fracture if necessary and selects a bone drill and drills a hole in accordance with conventional techniques. The diameter of the hole may be slightly larger than the diameter of the distal anchor 34. If the injury is a fracture, the hole preferably extends up to or slightly beyond the fracture. Preferably, the device is self-tapping. Thus, the pre-drilling process described above is optional.

A fixation device 200 having an axial length and outside diameter suitable for the hole is selected. The distal end 32 of the fixation device 200 is advanced distally into the hole until the distal anchor 34 reaches the distal end of the hole. Preferably, the proximal anchor 204 is carried by the fixation device 200 prior to advancing the body 28 into the hole. However, it may be attached following placement of the body 28 within the hole. Once the body 28 and proximal anchor 204 are in place, the clinician may use a tool 400, 420 such as the one shown in FIG. 8 or FIG. 9A to rotate the proximal anchor 204 and thus cancellous bone anchor 34 into the bone. Any of a variety of other driving devices, such as electric drills or hand tools may also be used.

Once the anchor 34 is in the desired location, proximal traction is applied to the proximal end 30 of body 28. Preferably, a tool 400, 420 such as the ones shown in FIGS. 8 and 9B is used. The tool uses a ratcheting motion so that the fixation device is compressed (such as is shown in FIG. 2) without rotating the soft tissue 302. In this manner, the proximal anchor 204 is advanced distally until the anchor 204 fits snugly against the outer surface of the tissue adjacent the bone and the fracture is completely reduced. Appropriate tensioning of the fixation device 200 could be accomplished by tactile feedback or through the use of a calibration device for applying a predetermined load on the implantation device. One advantage of the structure of the present invention is the ability to adjust compression independently of the setting of the distal anchor 34. Conventional hemostats, pliers or a calibrated loading device, could be used instead of or in combination with the tool 400, 420.

With many fractures or other injuries, a single fixation device 200 may be all that is clinically indicated. However, two or three or more fixation devices 200 may be utilized to reduce a single fracture, depending upon the location and physical requirements of the injury. The proximal end of the fixation devices 200 may be connected together such as through a three-holed plate or rod, or may be independent of each other.

The access site may be closed and dressed in accordance with conventional wound closure techniques. Preferably, such closure and dressing will be performed after the device is installed (FIG. 1), but prior to compression (shown in FIG. 2). In some embodiments (not shown) the flange 202 may include suture holes. In such embodiments, the device is inserted and compressed (as shown in FIG. 2). Sutures (through the suture holes) are inserted. Sutures can be inserted prior to or after insertion and compression.

FIG. 8 illustrates an exemplary tool 400 for installing a soft tissue fixation device 200. The tool 400 includes a gripping member 402 configured to mate with the recess 210 in the flange 202. The fixation device 200 is positioned over the tissue 300. The tool 400 is then used to rotate the tool until the fixation device 200 is installed in the bone 302 as shown in FIG. 1.

Once the fixation device is installed as shown in FIG. 1, the tool 400 can be used to ratchet the device so that the fixation device 200 is compressed and the flange is rotated, if desired, as shown in FIG. 2. As described above, the body 28 is recessed below the flange 202. Following the compression and flange adjustment (shown in FIG. 2), the body 28 remains recessed or is flush with the proximal surface 214 of the flange. In preferred embodiments, the proximal anchor 304 includes an extension portion 310 to allow for a greater compression range. This final compression and/or flange rotation does not rotate the tissue 300. This provides for a strong tissue fixation. In exemplary embodiments, the device cannot be moved (unless the entire fixation device 200 is removed) once the device is inserted.

FIGS. 9A and 9B illustrate an alternative fixation device 200 and installation tool 420 combination. The tool 420 shown in FIG. 9A does not include an integral gripping mechanism.

In this modified arrangement, a removable portion 422 may form a part of the driving device 420, which is used to rotate the proximal anchor 204 and thus cancellous bone anchor 34 into the bone. The removable portion 422 has one end which is configured to removably engage to insertion tool 420. For example, insertion tool 420 may include a recess sized and configured to engage with one end of the removable portion 422 of the insertion device 420. The second, opposing, end of the removable portion 422 of the installation device 420 is sized and configured to be removably engaged to the fixation device 200. As described herein, the flange 200 of the fixation device 200 may include a recess 210 with which the end of the removable portion 422 of the insertion device 420 may be removably engaged. The removable portion 422 is used to apply proximal traction so as to compress the fracture. After appropriate tensioning, the removable portion 422 can be de-coupled from the fixation device 200 and removed with the driving device 420.

In the foregoing variation, the removable portion 422 may be connected to a rotatable control such as a thumb wheel on the deployment device. A container may be opened at the clinical site exposing the proximal end of the implant, such that the distal end of the removable portion 422 may be removably coupled thereto. Proximal retraction of the hand tool 420 will pull the implant out of its packaging. The implant may then be positioned within the aperture in the bone, rotated to set the distal anchor, and the hand piece may be manipulated to place proximal traction on the removable portion 422 while simultaneously distally advancing the proximal anchor. Following appropriate tensioning across the fracture, the removable portion 422 may be disengaged from the implant, and removed from the patient. In the example of a threaded engagement, the removable portion 422 may be disengaged from the implant by rotating a thumb wheel or other rotational control on the hand piece. In an alternate embodiment, such as where the removable portion 422 comprises a pull wire, following appropriate tensioning across the fracture, a first end of the pull wire is released such that the pull wire may be removed from the implant by proximal retraction of the second end which may be attached to the hand piece.

Preferably, the clinician will have access to an array of fixation devices 200, having, for example, different diameters, axial lengths and, if applicable, angular relationships. These may be packaged one per package in sterile envelopes or peelable pouches, or in dispensing cartridges which may each hold a plurality of devices 200. Upon encountering an injury for which the use of a fixation device is deemed appropriate, the clinician will assess the dimensions and load requirements, and select a fixation device 200 from the array, which meets the desired specifications.

The fixation devices of the present invention may be made from either conventional bioabsorbable materials or conventional non-absorbable materials, combinations thereof and equivalents thereof. In addition, natural materials such as allografts may be used. Examples of absorbable materials include homopolymers and copolymers of lactide, glycolide, trimethylene carbonate, caprolactone, and p-dioxanone and blends thereof. The following two blends may be useful: (1) the blend of poly(p-dioxanone) and a lactide/glycolide copolymer, as disclosed in U.S. Pat. No. 4,646,741 which is incorporated by reference and (2) the glycolide-rich blend of two or more polymers, one polymer being a high glycolide content disclosed in U.S. Pat. No. 4,889,119 which is incorporated by reference. Additional bioabsorbable materials are disclosed in U.S. Pat. No. 6,348,053, the disclosure of which is incorporated in its entirety herein by reference.

The fixation devices may also be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. Alternatively, the distal anchor comprises a bioabsorbable material, and the body and proximal anchor comprise either a bioabsorbable material or a non-absorbable material, connected by an absorbable link. This may be accomplished by providing a concentric fit between the distal anchor and the body, with a transverse absorbable pin extending therethrough. This embodiment will enable removal of the body following dissipation of the pin, while leaving the distal anchor within the bone.

The components of the invention (or a bioabsorbable polymeric coating layer on part or all of the anchor surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

In addition, the components may be provided with any of a variety of structural modifications to accomplish various objectives, such as osteoincorporation, or more rapid or uniform absorption into the body. For example, osteoincorporation may be enhanced by providing a micropitted or otherwise textured surface on the components. Alternatively, capillary pathways may be provided throughout the body and collar, such as by manufacturing the anchor and body from an open cell foam material, which produces tortuous pathways through the device. This construction increases the surface area of the device which is exposed to body fluids, thereby generally increasing the absorption rate. Capillary pathways may alternatively be provided by laser drilling or other technique, which will be understood by those of skill in the art in view of the disclosure herein. In general, the extent to which the anchor can be permeated by capillary pathways or open cell foam passageways may be determined by balancing the desired structural integrity of the device with the desired reabsorption time, taking into account the particular strength and absorption characteristics of the desired polymer.

One open cell bioabsorbable material is described in U.S. Pat. No. 6,005,161 as a poly(hydroxy) acid in the form of an interconnecting, open-cell meshwork which duplicates the architecture of human cancellous bone from the iliac crest and possesses physical property (strength) values in excess of those demonstrated by human (mammalian) iliac crest cancellous bone. The gross structure is said to maintain physical property values at least equal to those of human, iliac crest, cancellous bone for a minimum of 90 days following implantation. The disclosure of U.S. Pat. No. 6,005,161 is incorporated by reference in its entirety herein.

In the embodiments described above, it should be appreciated that the distal anchor may be configured to be used with a pre-drilled hole and/or self tapping.

The components of the present invention may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

The specific dimensions of any of the bone fixation devices of the present invention can be readily varied depending upon the intended application, as will be apparent to those of skill in the art in view of the disclosure herein. Moreover, although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply difference other than those which may be expressly set forth. Accordingly, the present invention is intended to be described solely by reference to the appended claims, and not limited to the preferred embodiments disclosed herein.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A soft tissue anchor device, comprising:
   an elongate body, having a proximal end and a distal end;
   a helical anchor on the distal end;
   a retention structure on the body, proximal to the helical anchor;
   a proximal anchor, moveably carried by the elongate body wherein the proximal anchor is moveable in the distal direction with respect to the elongate body and the retention structure resists proximal movement of the proximal anchor with respect to the elongate body;
   an adjustable flange, the adjustable flange being configured to receive the proximal anchor, the proximal anchor configured to be rotational with respect to the flange, the adjustable flange configured to be positioned at a variable angle with respect to the elongate body; and
   a removable member comprising a first end configured to removably engage with the proximal end of the elongated body and a second end configured to removably engage with an installation tool.

2. The soft tissue anchor of claim 1, wherein, upon installation of the soft tissue anchor device, the soft tissue anchor attaches a soft tissue to a hard tissue and the flange retains the soft tissue anchor in the hard tissue preventing proximal or distal movement of the soft tissue anchor device.

3. The soft tissue anchor of claim 1, wherein the flange comprises a proximal surface and a distal surface having at least one spike protruding from the distal surface.

4. The soft tissue anchor device of claim 3, wherein the flange comprises a plurality of spikes protruding from the distal surface of the flange, the plurality of spikes being space around a perimeter of the flange.

5. The soft tissue anchor device of claim 4, wherein the plurality of spikes are spaced equidistantly relative to each other.

6. The soft tissue anchor device of claim 1, wherein the body is cannulated.

7. The soft tissue anchor device of claim 1, wherein the flange comprises a flange recess configured to be engageable with an installation tool.

8. The soft tissue anchor device of claim 1, wherein the elongate body is made of titanium.

9. The soft tissue anchor device of claim 1, wherein the elongate body has a length in a range of about 10 mm to about 80 mm.

10. The soft tissue anchor device of claim 1, wherein the elongate body has a diameter in a range of 2 mm to about 6 mm.

11. The soft tissue anchor device of claim 1, wherein the helical anchor has a major diameter in a range of about 3.5 mm to about 30 mm.

12. The soft tissue anchor device of claim 1, wherein the proximal anchor is split.

13. The soft tissue anchor device of claim 1, wherein the first end of the removable member is threaded.

14. A soft tissue anchor device, comprising:
an elongate body, having a proximal end and a distal end;
a distal anchor on the distal end;
retention structures on the body, proximal to the distal anchor;
a proximal anchor comprising complementary retention structures and a housing that defines a through-bore, wherein the elongate body extends through the through-bore such that the proximal anchor is moveably carried by the elongate body and wherein the retention structures and complementary retention structures are configured such that the proximal anchor is moveable in the distal direction with respect to the body while proximal movement of the proximal anchor with respect to the body is resisted;
an adjustable flange having a flanged recess configured to receive the proximal anchor, the proximal anchor configured to be rotational with respect to the flange, the adjustable flange configured to be positioned at a variable angle with respect to the body; and
a removable member comprising a first end configured to removably engage with the elongated body and a second end configured to removably engage with an installation tool.

15. The soft tissue anchor of claim 14, wherein the flange comprises proximal surface and a distal surface having at least one spike protruding from the distal surface.

16. The soft tissue anchor of claim 14, wherein the retention structures and complementary retention structures are configured such that the proximal anchor is moveable in the distal direction with respect to the elongate body without rotation of the proximal anchor with respect to the elongate body.

17. The soft tissue anchor device of claim 13, wherein the first end of the removable member is threaded.

* * * * *

UNITED STATES PATENT AND TRADEMARK OFFICE
CERTIFICATE OF CORRECTION

| | | |
|---|---|---|
| PATENT NO. | : 7,175,625 B2 | Page 1 of 1 |
| APPLICATION NO. | : 10/719086 | |
| DATED | : February 13, 2007 | |
| INVENTOR(S) | : Culbert | |

It is certified that error appears in the above-identified patent and that said Letters Patent is hereby corrected as shown below:

Column 3, line 41, delete "and or" and insert -- and/or --, therefore.
Column 5, line 32, after "202" please insert -- ) --, therefore.
Column 12, line 20 (approx.), in Claim 15, after "comprises" insert -- a --.
Column 12, line 29 (approx.), in Claim 17, please delete "13," and insert -- 14, --, therefore.

Signed and Sealed this

Tenth Day of July, 2007

JON W. DUDAS
*Director of the United States Patent and Trademark Office*